United States Patent [19]

Kakamura et al.

[11] Patent Number: 5,338,850
[45] Date of Patent: Aug. 16, 1994

[54] PYRIDINIUM DERIVATIVES

[75] Inventors: Ko Kakamura; Toshikazu Hochi; Kazuhara Ienaga, all of Hyogo, Japan

[73] Assignee: Nippon Zoki Pharmaceutical Co., Ltd., Osaka, Japan

[21] Appl. No.: 35,619

[22] Filed: Mar. 23, 1993

[30] Foreign Application Priority Data

Mar. 24, 1992 [JP] Japan .................................. 4-100394
Jun. 24, 1992 [JP] Japan .................................. 4-191649

[51] Int. Cl.$^5$ ..................... C07D 471/04; G01N 33/53
[52] U.S. Cl. ..................... 546/122; 436/518; 436/536; 436/547; 436/822; 530/389.8
[58] Field of Search ................. 546/122; 436/518, 536, 436/547, 822; 530/389.8

[56] References Cited

PUBLICATIONS

Nakamura et al., J. Chem. Soc., Chem. Communications, (14) pp. 992–994 (Jul. 1, 1992).

*Primary Examiner*—Bernard Dentz
*Attorney, Agent, or Firm*—Fisher, Christen & Sabol

[57] ABSTRACT

The present invention provides novel pyridinium derivatives which are effective, for example, in diagnosis of diabetes, diabetic complications, aging, diseases accompanied by aging, etc. and also provides an antibody prepared from said derivative as a hapten.

The pyridinium derivatives of the present invention are novel compounds represented by the following general formulae:

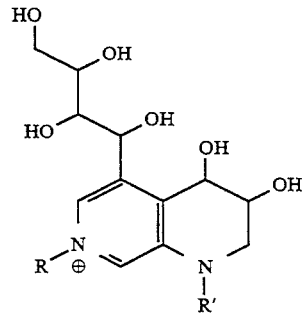

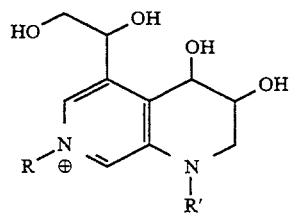

wherein R and R' may be the same or different and are optionally substituted alkyl groups, and their pharmaceutically acceptable salts.

It is possible to conduct the diagnosis of diabetes, diabetic complications, aging, diseases accompanied by aging, etc. using a compound of the present invention as an indicator. Moreover, it is possible to utilize a compound of the present invention for the evaluation of the pharmaceutical effect of pharmaceuticals effective for diabetes-related diseases, aging and diseases accompanied by aging.

19 Claims, No Drawings

PYRIDINIUM DERIVATIVES

FIELD OF THE INVENTION

The present invention relates to novel pyridinium derivatives; an antibody prepared from said derivative as a hapten; a method for diagnosis of diabetes, diabetic complications, aging, diseases accompanied by aging, etc. using said derivative or antibody thereof; and a method for evaluation of effects of pharmaceuticals which are effective for such diabetes-related diseases, aging and diseases which accompany old age.

BACKGROUND OF THE INVENTION

In 1968, glycosylhemoglobin (HbAlc) which is one of the minor components of hemoglobin was identified in vivo and was found to increase in patients diagnosed with diabetes. This discovery has aroused interest in the biological meaning of the Maillard reaction and, particularly, in the relationship between aging and diabetes.

The Maillard reaction may be classified into a former stage and latter stage. In the former stage a Schiff base is formed by the condensation reaction between an amino group of a protein and an aldehyde group of a reducing sugar. The Schiff base is stabilized as a result of an Amadori rearrangement. In the latter stage, the former stage product undergoes a long series of reactions, to obtain the latter-stage products of the Maillard reaction. The latter stage products are characterized by fluorescence, a color change to brown, and molecular crosslinking. The fluorescence, which is known as one of the characteristic changes found in the latter-stage products of the Maillard reaction, is significantly higher in diabetic patients than in healthy or non-diabetic persons. The fluorescence is suggested to have a correlation with the onset of diabetic complications such as diabetic nephrosis, arteriosclerosis, nervous disturbance, retinal diseases, cataracts, etc.

However, basic structures for the latter-stage products of the Maillard reaction have not been clarified yet. Accordingly, there have been many ambiguous points with respect to mechanisms for the nonenzymatic saccharization and crosslinking of proteins caused by aging and diabetes.

The present inventors have conducted continued studies on the mechanisms of nonenzymatic saccharization and crosslinking of proteins and, as a result thereof, found novel pyridinium derivatives which relate to the basic structure of the latter-stage products of the Maillard reaction. The pyridinium derivatives of the present invention are useful in the diagnosis of diabetes, diabetic complications, aging, and diseases associated with aging. The pyridinium derivatives are also useful for the evaluation of the effectiveness of pharmaceuticals for treatment of diabetes, diabetes related diseases, aging and its accompanying diseases.

SUMMARY OF THE INVENTION

The present invention provides: a) novel pyridinium derivatives and salts thereof, b) an antibody prepared from said derivative as a hapten, c) a method for the diagnosis of diabetes, diabetic complications, aging, diseases accompanied by aging, etc. using said derivative, or an antigen or antibody of said derivative, and d) a method for the evaluation of the effectiveness of pharmaceuticals for treatment of diabetes, diabetes-related diseases, aging, diseases accompanied by aging, etc.

Chemical structures of the pyridinium derivatives of the present invention are believed to be related to the chemical structures of the latter-stage products of the Maillard reaction. The derivatives are useful for detecting Maillard reaction type products associated, for example, with diabetes and aging.

For example, the antibodies of the present invention may be prepared by reacting a pyridinium derivative with a carrier protein to stimulate antibody production in vivo. The antibodies thus produced may be used to detect antigens or latter-stage, fluorescent Maillard reaction type products associated with or resulting from diabetes, diabetic complications, aging, and diseases associated with aging. The pyridinium derivatives of the present invention may be used to detect antibodies associated with diabetes or aging, or diseases which accompany diabetes or aging. Evaluation of the effectiveness of pharmaceuticals or therapeutic agents for the treatment or prevention of these ailments may be performed, for example, by using the antibodies of the present invention to detect any decreases or increases in the amount of antigens or latter stage Maillard reaction type products which result from the treatment.

The pyridinium derivatives of the present invention are represented by the structural formula:

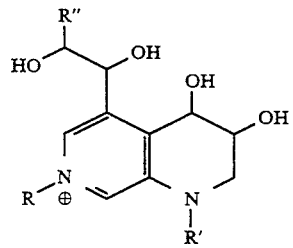

wherein R and R' may be the same or different and are unsubstituted or substituted alkyl groups, and R" is hydrogen or a 1, 2 dihydroxyethyl group, and pharmaceutically acceptable salts thereof. The preferred substituted alkyl groups are alkyl groups substituted with at least one member selected from the group consisting of amino, protected amino, and carboxyl groups.

Derivatives of the present invention may be produced by a process comprising combining a compound of the formula R—$NH_2$ (wherein R and R' have the same meaning as described above) with a hexose or an oligosaccharide consisting of at least one hexose to obtain a mixture, and permitting the mixture to stand for a sufficient amount of time to obtain one or more of the derivatives, and recovering the derivatives from the reaction mixture.

DETAILED DESCRIPTION OF THE INVENTION

Novel pyridinium derivatives of the present invention are the compounds represented by the following general formula (I) or (II):

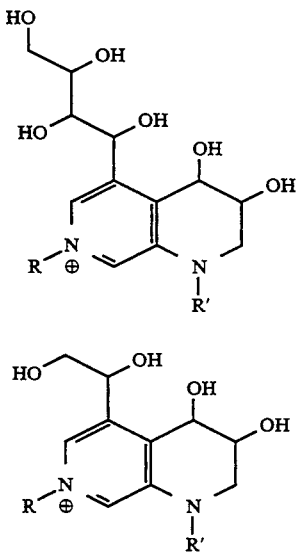

wherein R and R' may be the same or different and represent an optionally substituted alkyl group, as well as pharmaceutically acceptable salts of the derivatives.

The optionally substituted alkyl groups R and R' in the above general formula (I) and (II) may be acyclic and may have a linear or branched structure. The alkyl groups may also be cycloalkyl groups. Examples of the preferred alkyl for R and R' in the above general formula (I) or (II) are linear or branched alkyl groups or cycloalkyl groups having 1 to 6 carbon atom(s) such as methyl, ethyl, propyl, isopropyl, butyl, isobutyl, sec-butyl, tert-butyl, cyclobutyl, pentyl, isopentyl, neopentyl, tert-pentyl, cyclopentyl, hexyl and cyclohexyl groups.

The alkyl groups represented by R and R' may be substituted alkyl groups, that is they may be alkyl groups as described above which further contain one or more functional groups. Among the functional groups, amino, protected amino and/or carboxyl substituents are preferred. With regard to the protective groups for the amino group, those which are commonly used in the field of peptide synthesis, etc. may be utilized. They are for example, acetyl, benzyloxycarbonyl, p-methoxybenzyloxycarbonyl, p-chlorobenzyloxycarbonyl, p-nitrobenzyloxycarbonyl, p-phenylazobenzyloxycarbonyl, p-methoxyphenylazobenzyloxycarbonyl, tert-butoxycarbonyl, tert-amyloxycarbonyl, p-biphenylisopropyloxycarbonyl, diisopropropylmethyloxycarbonyl and formyl.

The pyridinium derivatives of the present invention include salts of the compounds represented by the general formula (I) or (II). The salts include pharmaceutically acceptable salts with at least one metal, acid, or base. Exemplary salts are alkali metal salts such as sodium, potassium and lithium salts; alkaline earth metal salts such as magnesium, calcium and barium salts; and salts of other metals such as aluminum. Further examples are addition salts with acids such as hydrochloric acid, sulfuric acid, nitric acid, phosphoric acid, formic acid, acetic acid, citric acid, lactic acid, hydrobromic acid and trifluoroacetic acid; and salts of ammonia or of organic bases such as amines.

The salts of the present invention can be manufactured by conventional methods from the pyridinium derivatives of the present invention in free form and vice versa.

When stereoisomers such as cis-trans isomers, optical isomers and conformational isomers exist in the compounds of the present invention, the present invention includes any of the isomers.

The compounds of the present invention may be produced, for example, by reacting a compound of the formula R—NH2 or R'—NH2 (wherein R and R' are the same groups as described above) with a hexose such as glucose, fructose, galactose or mannose, or an oligosaccharide consisting of the said hexose, to obtain the compound of the present invention. There is no particular restriction for the reaction conditions such as reaction temperature, reaction time, pH, etc. For example, the reaction can be conducted at room temperature and atmospheric pressure or accelerated by heating. Temperatures up to about 40° C. for about three to six weeks may, for example, be used to obtain the compounds of the present invention.

The compounds of the present invention prepared as such may be purified by common means such as distillation, chromatography, recrystallization, etc. and identified by means of NMR, mass analysis, fluorescence spectrum, etc.

The present invention is further illustrated by the following examples wherein all parts, percentages, and ratios are by weight and all temperatures are in °C. unless otherwise indicated:

EXAMPLE 1

Pentylamine (25 ml) and 38.7 g of glucose were dissolved in 1 liter of 250 mM phosphate buffer (pH: 7.4) and allowed to stand at 37° C. for 3 weeks.

The reaction solution was washed with 500 ml of ethyl acetate twice and the resulting aqueous layer was added to a column of Amberlite XAD-2 followed by thorough washing with water. The fraction eluted by methanol containing 10% of acetic acid was concentrated, the concentrate was dissolved in water and the solution was washed with ethyl acetate again. This was acidified with concentrated hydrochloric acid, extracted with n-butanol and the extract was added to a column of Amberlite XAD-2. Acetic acid (20%) was poured down the column and the fractions containing a fluorescent substance were combined and concentrated. This was added to a column of the reversed phase type, washed and eluted with a mixture of methanol and trifluoroacetic acid to give 1.8 g of oil. This was purified by separation by means of high performance liquid chromatography to give 450 mg of the compound 1; 350 mg of the compound 2; 50 mg of the compound 3; and 30 mg of the compound 4 separately, all identified below. Each of the compounds was converted to its hydrochloride salt.

EXAMPLE 2

α-Acetyllysine hydrochloride (44.9 g) was made to react with 36 g of glucose by allowing the mixture to stand at 37° C. for 6 weeks in accordance with the same manner as used in Example 1. The reaction solution was not concentrated but just added to an ion exchange resin of the sulfonate type, thoroughly washed with water and eluted with 2N aqueous ammonia. The fraction was concentrated, separated/purified using the same resin as used in Example 1 (wherein a mixture of methanol and trifluoroacetic acid was used) and converted to hydrochlorides to afford 37 mg of a pale yellow and syrupy compound 5; 26 mg of the compound 6; and several mg of the compounds 7 and 8, all identified below.

The same procedures were conducted as above using γ-aminobutyric acid and β-alanine to give the compounds 9 to 17, all identified below.

EXAMPLE 3

Instead of glucose, fructose was mixed with pentylamine and the same procedures were conducted as in Example 1 above. As a result of this reaction, the compounds 1 to 4 were obtained similarly as in Example 1.

The physical properties of the resulting compounds 1 to 17 in accordance with the present invention are:

Compound 1: (3R,4S)-3,4-Dihydroxy-5-{1-[(1S,2S,3R)-1,2,3,4-tetrahydroxybutyl]}-1,7-dipentyl-1,2,3,4-tetrahydro-[1,7]naphthyridinium
  Fluorescence spectrum: Em=380 nm, Ex=463 nm
  Mass analysis (SIMS, Glycerol): M+(m/z)=427.

Compound 2: (3R,4S)-3,4-Dihydroxy-5-{1-[(1R,2S,3R)-1,2,3,4-tetrahydroxybutyl]}-1, 7-dipentyl-1,2,3,4-tetrahydro-[1,7]naphthyridinium
  Fluorescence spectrum: Em=379 nm, Ex=464 nm
  Mass analysis (SIMS, Glycerol): M+(m/z)=427.

Compound 3: (3R,4S)-3,4-Dihydroxy-5-{1-[(1S)-1,2,-dihydroxyethyl]}-1,7-dipentyl-1,2,3,4-tetrahydro-[1,7]naphthynidinium
  Fluorescence spectrum: Em=380 nm, Ex=464 nm
  Mass analysis (SIMS, Glycerol): M+(m/z)=367.

Compound 4: (3R,4S)-3,4-Dihydroxy-5-}1-[(1R)-1,2,-dihydroxyethyl]}-1,7-dipentyl-1,2,3,4-tetrahydro-[1,7]naphthynidinium
  Fluorescence spectrum: Em=380 nm, Ex=462 nm
  Mass analysis (SIMS, Glycerol): M+(m/z)=367

Compound 5: (3R,4S)-3,4-Dihydroxy-5-}1-[(1S, 2S, 3R-1,2,3,4-tetrahydroxybutyl]}-1,7-di[6-(N-acetyl-L-norleucyl)]-1,2,3,4-tetrahydro-[1,7]naphthynidinium
  Fluorescence spectrum: Em=379 nm, Ex=461 nm
  Mass analysis (SIMS, Glycerol): M+(m/z)=629

Compound 6: (3R,4S)-3,4-Dihydroxy-5-{1-[(1R, 2S,3R)-1,2,3,4-tetrahydroxybutyl]}-1,7-di[6-(N-acetyl-L-norleucyl)]-1,2,3,4-tetrahydro-[1,7]naphthynidinium
  Fluorescence spectrum: Em=377 nm, Ex=461 nm
  Mass analysis (SIMS, Glycerol): M+(m/z)=629

Compound 7: (3R,4S)-3,4-Dihydroxy-5-{1-[(1S)-1,2,-dihydroxyethyl]}-1,7-di(6-(N-acetyl-L-norleucyl)]-1,2,3,4-tetrahydro-[1,7]naphthynidinium
  Fluorescence spectrum: Em=379 nm, Ex=461 nm
  Mass analysis (SIMS, Glycerol): M+(m/z)=569

Compound 8: (3R,4S)-3,4-Dihydroxy-5-{1-[(1R)-1,2,dihydroxyethyl]}-1,7-di(6-(N-acetyl-L-norleucyl)]-1,2,3,4-tetrahydro-[1,7]naphthynidinium
  Fluorescence spectrum: Em=378 nm, Ex=462 nm
  Mass analysis (SIMS, Glycerol): M+(m/z)=569

Compound 9: (3R,4S)-3,4-Dihydroxy-5-{1-[(1S,2S,3R)-1,2,3,4-tetrahydroxybutyl]}-1,7-di(3-carboxypropyl)-1,2,3,4-tetrahydro-[1,7]naphthyridinium
  Fluorescence spectrum: Em=380 nm, Ex=464 nm
  Mass analysis (SIMS, Glycerol): M+(m/z)=443

Compound 10: (3R,4S)-3,4-Dihydroxy-5-{1-[(1R,2S,3R)-1,2,3,4,-tetrahydroxybutyl]}-1,7-di(3-carboxypropyl)-1,2,3,4-tetrahydro-[1,7]naphthyridinium
  Fluorescence spectrum: Em=379 nm, Ex=463 nm
  Mass analysis (SIMS, Glycerol): M+(m/z)=443

Compound 11: (3R,4S)-3,4-Dihydroxy-5-{1-[(1S)-1,2-dihydroxyethyl]}-1,7-di (3-carboxypropyl)-1,2,3,4-tetrahydro-[1,7]naphthyridinium
  Fluorescence spectrum: Em=380 nm, Ex=462 nm
  Mass analysis (SIMS, Glycerol): M+(m/z)=383

Compound 12: (3R,4S)-3,4-Dihydroxy-5-{1-[(1R)-1,2-dihydroxyethyl]}-1,7-di (3-carboxypropyl)-1,2,3,4-tetrahydro-[1,7]naphthyridinium
  Fluorescence spectrum: Em=380 nm, Ex=463 nm
  Mass analysis (SIMS, Glycerol): M+(m/z)=383

Compound 13: (3R,4S)-3,4-Dihydroxy-5-{1-[(1S,2S,3R)-1,2,3,4-tetrahydroxybutyl]}-1,7-di(2-carboxyethyl)-1,2,3,4-tetrahydro-[1,7]naphthyridinium
  Fluorescence spectrum: Em=379 nm, Ex=463 nm
  Mass analysis (SIMS, Glycerol): M+(m/z)=429

Compound 14: (3R,4S)-3,4-Dihydroxy-5-{1-[(1R,2S,3R)-1,2,3,4-tetrahydroxybutyl]}-1,7-di(2-carboxyethyl)-1,2,3,4-tetrahydro-[1,7]naphthynidinium
  Fluorescence spectrum: Em=379 nm, Ex=464 nm
  Mass analysis (SIMS, Glycerol): M+(m/z)=429

Compound 15: (3R,4S)-3,4-Dihydroxy-5-{1-[(1S)-1,2-dihydroxyethyl]}-1,7-di(2-carboxyethyl)-1,2,3,4-tetrahydro[1,7]naphthynidinium
  Fluorescence spectrum: Em=380 nm, Ex=463 nm
  Mass analysis (SIMS, Glycerol): M+(m/z)=369

Compound 16: (3R,4S)-3,4-Dihydroxy-5-{1-[(1R)-1,2-dihydroxyethyl]}-1,7-di(2-carboxyethyl)-1,2,3,4-tetrahydro-[1,7]naphthynidinium
  Fluorescence spectrum: Em=378 nm, Ex=462 nm
  Mass analysis (SIMS, Glycerol): M+(m/z)=369

Compound 17: Epimer of the compound 9 with respect to carbon atom 3.

Tables 1 to 3 show some examples of the analytical results obtained with $^1$H-NMR (400 MHz, CD$_3$OD) and $^{13}$C-NMR (100 MHz, CD$_3$OD). TMS was used as an internal standard and assignments in $^{13}$C-NMR were based upon the results of measurements of "C-H COSY" and "COLOC". Values in parentheses are coupling coefficients. The assignments marked with !, !!, * and ** have a possibility of replacing each other.

TABLE 1

| | Compound 1 | | Compound 2 | |
|---|---|---|---|---|
| C # | $^{13}$C | $^1$H | $^{13}$C | $^1$H |
| 2 | 49.9 t | 3.37 ddd (1, 1, 13) | 50.0 t | 3.37 ddd (1, 1, 13) |
| | | 3.68 dd (2, 13) | | 3.69 dd (2, 13) |
| 3 | 65.6 d | 4.03 ddd (1, 2, 3) | 66.1 d | 4.02 ddd (1, 2, 3) |
| 4 | 62.8 d | 4.77 dd (1, 3) | 63.4 d | 4.73 dd (1, 3) |
| 4a | 132.9 s | | 133.2 s | |
| 5 | 145.0 s | | 145.5 s | |
| 6 | 130.9 d | 8.09 br. s | 131.4 d | 8.14 br. s |
| 8 | 125.2 d | 8.09 br. s | 124.8 d | 8.09 br. s |
| 8a | 144.5 s | | 144.6 s | |
| 9 | 67.3 d | 5.64 br. s | 67.8 d | 5.53 br. s |
| 10 | 75.2 d | 3.50 br. d (9) | 74.9 d | 3.84 dd (1, 9) |
| 11 | 72.9 d | 3.84 m | 73.6 d | 3.85 m |
| 12 | 65.0 t | 3.68 dd (6, 12) | 65.1 t | 3.66 dd (5, 11) |
| | | 3.84 dd (3, 12) | | 3.83 dd (3, 11) |
| 1' | 52.3 t | 3.41 m | 52.5 t | 3.42 m |
| | | 3.54 m | | 3.58 m |
| 2' | 26.6 t | 1.66 m 2H | 26.7 t | 1.66 m 2H |
| 3' | 29.3 t | 1.3~1.45 m 2H | 29.4 t | 1.3~1.45 m 2H |
| 4' | 23.3 t | 1.3~1.45 m 2H | 23.3 t | 1.3~1.45 m 2H |
| 5' | 14.4 q | 0.94 t (7) 3H | 14.4 q | 0.94 t (7) 3H |
| 1" | 63.2 t | 4.49 t (7) 2H | 63.2 t | 4.49 t (7) 2H |
| 2" | 32.3 t | 1.99 m 2H | 32.4 t | 2.00 m 2H |
| 3" | 30.1 t | 1.3~1.45 m 2H | 30.1 t | 1.3~1.45 m 2H |
| 4" | 23.8 t | 1.3~1.45 m 2H | 23.8 t | 1.3~1.45 m 2H |
| 5" | 14.6 q | 0.94 t (7) 3H | 14.6 q | 0.95 t (7) 3H |

TABLE 2

| | Compound 3 | | Compound 4 | |
|---|---|---|---|---|
| C # | $^{13}$C | $^1$H | $^{13}$C | $^1$H |
| 2 | 50.0 t | 3.37 ddd (1, 1, 13) | 50.0 t | 3.37 (1, 1, 13) |
| | | 3.68 dd (2, 13) | | 3.66 dd (2, 13) |
| 3 | 65.7 d | 4.03 ddd (1, 2, 3) | 65.7 d | 4.05 ddd (1, 2, 3) |

TABLE 2-continued

| C # | Compound 3 $^{13}C$ | Compound 3 $^{1}H$ | Compound 4 $^{13}C$ | Compound 4 $^{1}H$ |
|---|---|---|---|---|
| 4 | 63.3 d | 4.76 dd (1, 3) | 63.7 d | 4.69 dd (1, 3) |
| 4a | 133.8 s | | 134.1 s | |
| 5 | 144.6 s | | 144.6 s | |
| 6 | 130.0 d | 8.10 br. s | 130.2 d | 8.12 br. s |
| 8 | 125.4 d | 8.09 br. s | 125.1 d | 8.10 br. s |
| 8a | 144.1 s | | 144.6 s | |
| 9 | 69.9 d | 5.28 dd (4, 6) | 69.9 d | 5.18 t (5) |
| 10 | 67.7 t | 3.65 dd (6, 12) | 67.6 t | 3.79 d (5) 2H |
|    |         | 3.78 dd (4, 12) |         |                |
| 1' | 52.3 t | 3.42 m | 52.4 t | 3.42 m |
|    |        | 3.55 m |        | 3.55 m |
| 2' | 26.6 t | 1.66 m 2H | 26.6 t | 1.66 m 2H |
| 3' | 29.3 t | 1.3~1.45 m 2H | 29.3 t | 1.3~1.45 m 2H |
| 4' | 23.2 t | 1.3~1.45 m 2H | 23.2 t | 1.3~1.45 m 2H |
| 5' | 14.2 q | 0.93 t (7) 3H | 14.2 q | 0.93 t (7) 3H |
| 1" | 63.1 t | 4.48 t (7) 2H | 63.2 t | 4.49 t (7) 2H |
| 2" | 32.3 t | 1.98 m 2H | 32.3 t | 1.98 m 2H |
| 3" | 30.0 t | 1.3~1.45 m 2H | 30.0 t | 1.3~1.45 m 2H |
| 4" | 23.7 t | 1.3~1.45 m 2H | 23.7 t | 1.3~1.45 m 2H |
| 5" | 14.4 t | 0.94 t (7) 3H | 14.4 q | 0.94 t (7) 3H |

TABLE 3

| C # | Compound 5 $^{13}C$ | Compound 5 $^{1}H$ | Compound 6 $^{13}C$ | Compound 6 $^{1}H$ |
|---|---|---|---|---|
| 2 | 49.9 t | 3.35 ddd (1, 1, 13) | 50.1 t | 3.37 (1, 1, 13) |
|   |        | 3.69 dd (2, 13) |        | 3.69 dd (2, 13) |
| 3 | 65.7 d | 4.03 ddd (1, 2, 3) | 66.1 d | 4.02 ddd (1, 2, 3) |
| 4 | 63.7 d | 4.77 dd (1, 3) | 63.4 d | 4.74 dd (1, 3) |
| 4a | 133.3 s | | 133.5 s | |
| 5 | 145.3 s | | 145.7 s | |
| 6 | 131.1 d | 8.09 br. s | 131.5 d | 8.15 br. s |
| 8 | 124.9 d | 8.08 br. s | 124.5 d | 8.07 br. s |
| 8a | 144.5 s | | 144.6 s | |
| 9 | 67.3 d | 5.64 br. s | 67.8 d | 5.53 br. s |
| 10 | 75.2 d | 3.51 br. d (9) | 74.9 d | 3.82 dd (1, 9) |
| 11 | 72.7 d | 3.84 m | 73.5 d | 3.86 m |
| 12 | 64.9 t | 3.70 dd (6, 12) | 65.0 t | 3.67 dd (5, 11) |
|    |        | 3.84 dd (3, 12) |        | 3.83 dd (3, 11) |
| 1' | 52.1 t | 3.40 m | 52.2 t | 3.40 m |
|    |        | 3.56 m |        | 3.56 m |
| 2' | 25.9 t | 1.70 m 2H | 25.9 t | 1.70 m 2H |
| 3' | *23.6 t | 1.50 m 2H | *23.6 t | 1.50 m 2H |
| 4' | **32.2 t | 1.7~2.0 m 2H | **32.2 t | 1.7~2.0 m 2H |
| 5' | 53.1 d | *4.40 dd (5, 9) | 53.2 d | 4.40 dd (5, 9) |
| 6' | !175.1 s | | !175.1 s | |
| Ac—Me | 22.5 q | **1.96 s 3H | 22.5 q | 1.96 s 3H |
| —CO | !!173.3 s | | !!173.3 s | |
| 1" | 62.9 t | 4.51 t (7) 2H | 63.0 t | 4.51 t (7) 2H |
| 2" | 31.9 t | 2.05 m 2H | 31.9 t | 2.05 m 2H |
| 3" | *23.9 t | 1.50 m 2H | *23.9 t | 1.50 m 2H |
| 4" | **32.6 t | 1.7~2.0 m 2H | **32.6 t | 1.7~2.0 m 2H |
| 5" | 53.1 d | *4.42 dd (5, 9) | 53.2 d | 4.42 dd (5, 9) |
| 6" | !175.4 s | | !175.3 s | |
| Ac—Me | 22.5 q | **1.99 s 3H | 22.5 q | 1.99 s 3H |
| —CO | !!173.4 s | | !!173.4 s | |

TABLE 4

| C # | Compound 9 $^{13}C$ | Compound 9 $^{1}H$ | Compound 10 $^{13}C$ | Compound 10 $^{1}H$ |
|---|---|---|---|---|
| 2 | 50.1 t | 3.40 ddd (1, 1, 13) | 50.2 t | 3.40 ddd (1, 1, 13) |
|   |        | 3.70 dd (2, 13) |        | 3.71 dd (2, 13) |
| 3 | 65.9 d | 4.04 ddd (1, 2, 3) | 66.3 d | 4.04 ddd (1, 2, 3) |
| 4 | 63.1 d | 4.78 dd (1, 3) | 63.7 d | 4.75 dd (1, 3) |
| 4a | 133.7 s | | 133.8 s | |
| 5 | 145.6 s | | 146.0 s | |
| 6 | 131.5 d | 8.33 br. s | 131.9 d | 8.32 br. s |
| 8 | 125.6 d | 8.13 br. s | 125.3 d | 8.17 br. s |
| 8a | 144.7 s | | 144.8 s | |
| 9 | 67.6 d | 5.65 d (1) | 68.0 d | 5.53 d (1) |
| 10 | 75.5 d | 3.50 dd (1, 9) | 75.2 d | 3.85 dd (1, 9) |
| 11 | 73.0 d | 3.85 m | 73.7 d | 3.86 m |
| 12 | 65.1 t | 3.71 dd (6, 12) | 65.2 t | 3.66 dd (5, 11) |
|    |        | 3.84 dd (3, 12) |        | 3.81 dd (3, 11) |
| 1' | 51.7 t | 3.46 m | 51.9 t | 3.45 m |

TABLE 4-continued

| C # | Compound 9 $^{13}C$ | Compound 9 $^{1}H$ | Compound 10 $^{13}C$ | Compound 10 $^{1}H$ |
|---|---|---|---|---|
|   |        | 3.55 m |        | 3.55 m |
| 2' | 21.5 t | 1.91 m 2H | 21.5 t | 1.89 m 2H |
| 3' | 31.1 t | 2.44 t (6) 2H | 31.2 t | 2.42 t (6) 2H |
| 4' | *175.7 s | | *175.9 s | |
| 1" | 62.7 t | 4.55 t (7) 2H | 62.7 t | 4.53 t (7) 2H |
| 2" | 27.9 t | 2.30 t (7) 2H | 27.9 t | 2.29 t (7) 2H |
| 3" | 31.4 t | 2.46 t (7) 2H | 31.4 t | 2.44 t (7) 2H |
| 4" | *177.2 s | | *177.2 s | |

TABLE 5

| C # | Compound 17 $^{13}C$ | Compound 17 $^{1}H$ |
|---|---|---|
| 2 | 50.0 t | 3.43 ddd (1, 1, 13) |
|   |        | 3.70 dd (2, 13) |
| 3 | 65.9 d | 4.02 ddd (1, 2, 3) |
| 4 | 63.1 d | 4.75 dd (1, 3) |
| 4a | 134.1 s | |
| 5 | 145.6 s | |
| 6 | 131.9 d | 8.32 br. s |
| 8 | 126.6 d | 8.20 br. s |
| 8a | 144.3 s | |
| 9 | 67.5 d | 5.64 d (1) |
| 10 | 75.4 d | 3.49 dd (1, 9) |
| 11 | 73.0 d | 3.84 m |
| 12 | 65.2 t | 3.69 dd (6, 13) |
|    |        | 3.83 dd (3, 13) |
| 1' | 48.3 t | 3.75 m |
|    |        | 3.82 m |
| 2' | 31.8 t | 2.71 m 2H |
| 3' | *173.4 s | |
| 4' | | |
| 1" | 58.9 t | 4.75 t (7) 2H |
| 2" | 36.1 t | 3.09 t (7) 2H |
| 3" | *175.4 s | |
| 4" | | |

Compounds 5 and 6 of the present invention were combined with a carrier protein, for example, bovine serum albumin, keyhole limpet hemocyanin (KLH) and the like, using water-soluble carbodiimide in accordance with the usual coupling reaction to prepare an antibody using the compounds 5 and 6 as haptens. Preparation of each antibody was conducted in rabbits by a method which is commonly used. The antibody prepared as such is capable of recognizing the compound of the present invention in vitro. The antibody is also capable of immunochemically discriminating the saccharized protein prepared in vitro and the crosslinked protein in the basement membrane of the glomerulus of model rats suffering from diabetic nephrosis induced by streptozotocin.

Among the compounds of the present invention represented by the general formula (I) or (II), pyridinium derivatives wherein R and R' are alkyl having amino and/or carboxyl can be easily combined with a carrier protein, etc. as haptens and are particularly useful, for the preparation of an antibody. As to a carrier for combining with a hapten for preparation of the antibody, the commonly-used carriers, such as protein (e.g. serum albumin, KLH) and polymers (e.g. polylsine) may be used. Especially, compounds 5 and 6 of the present invention are believed to exhibit a high relationship with the latter-stage products of the Maillard reaction in terms of chemical structures and, practically, they are of very high utility.

Accordingly, it is possible to conduct diagnosis of diabetes, diabetic complications (e.g. diabetic nephrosis, diabetic arteriosclerosis, diabetic nervous disturbance, diabetic cataracts, diabetic retinal diseases, diabetic minute blood vessel disturbance, etc.), aging and diseases accompanied by aging using the compounds of the present invention as an indicator. Moreover, it is possible to conduct an evaluation of the pharmaceutical effect in in vitro and in vivo systems using a compound of the present invention as an indicator. In addition, the antibody prepared from the compound of the present invention as a hapten can be utilized immunochemically and immunohistochemically in the abovementioned diagnosis and evaluation and are very useful.

We claim:

1. A pyridinium derivative represented by formula (I) or (II):

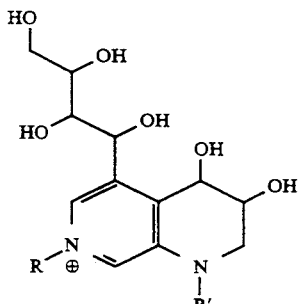

(I)

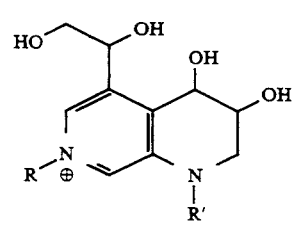

(II)

wherein R and R' may be the same or different and are optionally substituted alkyl groups, and pharmaceutically acceptable salts of the derivatives.

2. An antibody prepared from a pyridinium derivative as claimed in claim 1 as a hapter.

3. A pyridinium derivative as claimed in claim 1 wherein R and R' are the same.

4. A pyridinium derivative as claimed in claim 1 which is of formula I.

5. A pyridinium derivative as claimed in claim 1 wherein R and R' may be the same or different and are each an alkyl group or an alkyl group substituted with an amino group, a protected amino group and/or a carboxyl group, as well as pharmaceutically acceptable salts of the derivatives.

6. A pyridinium derivative as claimed in claim 1 wherein R and R' are each an alkyl group substituted with at least one member selected from the group consisting of amino, protected amino, and carboxyl groups.

7. A pyridinium derivative as claimed in claim 6 wherein said alkyl group has 1 to 6 carbon atoms.

8. (3R,4S)-3,4-Dihydroxy-5-{1-[1S,2S,3R-1,2,3,4-tetrahydroxybutyl]}-1,7-di[6-(N-acetyl-L-norleucyl)]-1,2,3,4-tetrahydro-[1,7]naphthyridinium.

9. (3R,4S)-3,4-Dihydroxy-5-{1-[(1R,2S,3R)-1,2,3,4-tetrahydroxybutyl]}-1,7-di[6-(N-acetyl-L-norleucyl)]-1,2,3,4-tetrahydro-[1,7]naphthyridinium.

10. A method for diagnosis of diabetes, diabetic complications, aging and diseases accompanied by aging comprising using a pyridinium derivative of claim 1 as an indicator.

11. A method for the diagnosis of diabetes, diabetic complications, aging and diseases accompanied by aging comprising using an antibody which is prepared from a pyridinium derivative of claim 1 as a hapten.

12. A method for the evaluation of the effectiveness of pharmaceuticals as therapeutic agents for diabetes, and for diabetic complications, as preventive agents for aging, and as therapeutic agents for diseases accompanied by aging comprising using a pyridinium derivative of claim 1 as an indicator.

13. A method for the evaluation of the effectiveness of pharmaceuticals as therapeutic agents for diabetes, and for diabetic complications, as preventive agents for aging and as therapeutic agents for diseases accompanied by aging comprising using an antibody which is prepared from the pyridinium derivative of claim 1 as a hapten.

14. A method for the diagnosis of diabetes and diabetic complications comprising detecting antigens or latter-stage, fluorescent Maillard reaction type products associated with or resulting from diabetes or diabetic complications with an antibody as claimed in claim 2.

15. A method for the evaluation of the effectiveness of a pharmaceutical for the treatment of diabetes or diabetic complications comprising detecting any changes caused by the treatment in the amount of antigens or latter stage fluorescent Maillard reaction type products which are associated with or result from diabetes or diabetic complications wherein said detection is achieved using an antibody of claim 2.

16. A method for the diagnosis of aging and diseases associated with aging comprising detecting antigens or latter-stage, fluorescent Maillard reaction type products associated with or resulting from aging or diseases associated with aging with an antibody as claimed in claim 2.

17. A method for the evaluation of the effectiveness of a pharmaceutical for the prevention of aging or as a therapeutic agent for diseases associated with aging comprising detecting any changes resulting from administration of said pharmaceutical in the amount of antigens or latter stage fluorescent Maillard reaction type products which are associated with or result from aging or diseases associated with aging wherein said detection is achieved using an antibody of claim 2.

18. An antibody obtained using a pyridinium derivative as claimed in claim 1 wherein the antibody is an indicator for the diagnosis of diabetes, diabetic complications, aging or diseases accompanied by aging, and is an indicator for the evaluation of the effects of pharmaceuticals or therapeutic agents for diabetes, diabetic complications, the effects of preventative agents for aging, or the effects of therapeutic agents for diseases accompanied by aging.

19. A process for the preparation of pyridinium derivatives as claimed in claim 1 comprising reacting at least one compound of the formula $R-NH_2$ or $R'-NH_2$, wherein R and R' may be the same or different and are unsubstituted alkyl groups or substituted alkyl groups, with a hexose or an oligosaccharide composed of one or more hexoses, said reaction being conducted for a sufficient amount of time to obtain at least one derivative as claimed in claim 1.

* * * * *